United States Patent [19]

Kosuna

[11] Patent Number: 5,756,318
[45] Date of Patent: May 26, 1998

[54] POLYSACCHARIDES AND PREPARATION THEREOF

[75] Inventor: Kenichi Kosuna, Sapporo, Japan

[73] Assignee: Amino Up Chemical Co., Ltd., Japan

[21] Appl. No.: 536,038

[22] Filed: Sep. 29, 1995

[30] Foreign Application Priority Data

Mar. 24, 1995 [JP] Japan ................................. 7-090042

[51] Int. Cl.$^6$ .................. C12P 19/04; C07H 1/00; C08B 37/00; C08B 37/18
[52] U.S. Cl. ............... 435/101; 536/123.12; 536/123.1; 536/124; 536/126; 536/102; 536/107
[58] Field of Search ................ 435/101; 536/123.12, 536/123.1, 124, 126, 102, 107

[56] References Cited

U.S. PATENT DOCUMENTS

| | | | |
|---|---|---|---|
| 4,051,314 | 9/1977 | Ohtsuka et al. | 536/1 |
| 4,162,939 | 7/1979 | Yoshikumi et al. | 435/254 |
| 4,200,693 | 4/1980 | Yokobayashi et al. | 435/101 |
| 4,501,888 | 2/1985 | Schmidt | 536/110 |
| 4,614,733 | 9/1986 | Yoshikumi et al. | 514/54 |
| 4,959,466 | 9/1990 | White | 536/119 |

OTHER PUBLICATIONS

Singleton, *Dictionary of Microbiology and Molecular Biology*, 2nd Ed. 1987, pp. 102–103.

*Primary Examiner*—Leon B. Lankford, Jr.
*Assistant Examiner*—Francisco C. Prats
*Attorney, Agent, or Firm*—Joseph C. Mason, Jr.

[57] ABSTRACT

A novel polysaccharide comprising (1->4) bonded α-D-glucose units represented by the following formula

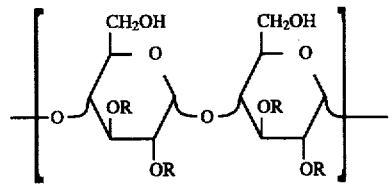

wherein R is a hydrogen atom or an acetyl group in a ratio of 7:3 is extracted and isolated from a liquid culture medium of a microorganism belonging to the class Basidiomycetes in the presence of a plant tissue extract. About 30% by mole of hydroxyl groups at the 2,3-positions of each unit is acetylated and the polysaccharide has a molecular weight of 500 to 10,000. The polysaccharide has properties of biological response modifiers (BRM) and is useful as an immuno-enhancing agent or immuno-activator.

7 Claims, No Drawings

POLYSACCHARIDES AND PREPARATION THEREOF

TECHNICAL FIELD

The present invention relates to novel polysaccharides originated from culture broth of liquid culture including a mixture of a culture medium containing plant tissues and the mycelia of microorganisms belonging to the class Basidiomycetes and isolated and purified therefrom. The polysaccharides have a molecular weight from 500 to 10,000 that are comprised by lineally (1→4) linked α-D-glucose units whose 2,3-hydroxyl groups are partially acetylated in a ratio of about 30%.

BACKGROUND ART

Recently, in the immunological therapy of cancers, there has been used the concept of biological response modifiers (BRM) which generally refers to substances that are expected to control the innate defense mechanisms of patients' bodies, i.e., immunity, and exhibit therapeutic effects on various diseases. Important examples thereof include bacteria-derived substances such as BCG (Bacillus Calmette-Guerin), and Picibanil, e.g., Picibanil OK-432, fungi-derived substances such as lentinan and schizophyllan, and synthetic substances such as pyran copolymers and levamisole. Representative examples of the BRM include lentinan that is isolated physicochemically highly purified and characterized. Lentinan is a substance isolated from the fruit bodies of *Lentinus edodes*. This compound is a glucan having a molecular weight of 400,000 to 800,000, consisting basically of a chain of β-D-glucose units which are mutually connected at the 3- and 6- positions in a ratio of 5:2, respectively. As for the biological activity, this compound is known to stimulate the maturing, differentiation, and propagation of cells which are important to innate defense mechanisms. More particularly, they give the power of resistance against cancers, infections, and the like, so that they are effective against such diseases.

Except for the above-mentioned lentinan, many anti-tumor, immuno-enhancing compounds, such as schizophyllan and grifolan, most of which are higher-molecular-weight β-1,3-glucans, have been isolated from microorganisms belonging to the class Basidiomycetes.

From the viewpoint of examining the quality of raw materials and increasing the yield, the object of the present invention is to extract and isolate novel polysaccharides having more potent immuno-enhancing abilities from the cultures of Basidiomycetes microorganisms grown by liquid culturing.

SUMMARY OF THE INVENTION

The present inventors have already filed a patent application on the method of preparing a biologically active hemicellulose in which a plant tissue raw material is assimilated in a culture medium for a filamentous fungus (Japanese Patent Application Laying-open No. 1-153701). Their further investigation has been continued in order to isolate active compounds involved in the essential mechanism of physiological activity. As a result, it has now been successful to isolate and purify a novel polysaccharide having a physiological activity (active polysaccharide, hereafter sometimes abbreviated as "APS") from the culture medium in which microorganisms belonging to the class Basidiomycetes are cultured in the presence of plant tissues as a raw material, thus completing the present invention.

Therefore, the present invention provides:
1) A novel polysaccharide (APS), comprising (1→4) bonded α-D-glucose units represented by the following formula

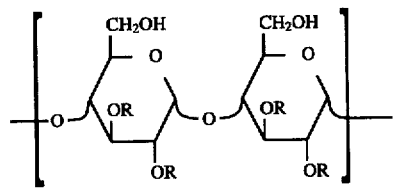

wherein R is a hydrogen atom or an acetyl group in the ratio of 7:3. The following are physicochemical properties:

(1) Nature: a white amorphous powder, without taste and odor;

(2) Solubility: insoluble in alcohol, acetone, hexane, benzene, ethyl acetate, tetrachloromethane, chloroform and ether, and soluble in water, formamide, and dimethylsulfoxide;

(3) pH of aqueous solution: neutral;

(4) Component sugar: glucose only;

(5) Molecular weight: 500 to 10,000;

(6) Specific optical rotation: $[\alpha]_D(24°\ C.)=+112°$ to $+116°$ (in water);

(7) Color reaction: positive to anthrone-sulfuric acid reaction, phenol-sulfuric-acid reaction, and chromotropic acid-sulfuric acid reaction, and negative to biuret reaction, Lowry-Folin reaction, Elson-Morgan reaction, and iodo reaction;

(8) Melting point: showing no clear melting point;

(9) IR spectrum: absorption specific to acetyl groups;

(10) $^{13}$C-NMR spectrum: exhibiting signals specific to α-1,4-glucan and acetyl groups; and 2) A method of preparing APS described above.

The APS, unlike conventional lentinan and schizophyllan, consists of (1→4) bonded α-D-glucose units exclusively, with about 30% of acetyl groups at the 2,3-hydroxyls. The polysaccharide has a molecular weight of 500 to 10,000, preferably 1,000 to 7,000, as measured by gel filtration column chromatography. The polysaccharide can be extracted and isolated from a broth or a mixture of culture medium and mycelia of a microorganism belonging to the class Basidiomycetes in a liquid culture in the presence of plant tissues as a raw material for culture medium.

DETAILED DESCRIPTION OF THE INVENTION

Hereinafter, the present invention is described in more detail.

The microorganisms or species of Basidiomycetes which can be used in the present invention include, for example, *Lentinus edodes, Agaricus bisporus, Grifola frondosa, Pholiota nameko, Pleurotus ostreatus, Flammulina velutipes, Ganoderma lucidum, Auricularia auricular, Ganoderma applanatum, Coriolus versicolor, Grifola umbellata, Schizophyllum commune, Volvariella volvacea,* and the like. These can be used singly or as combined forms.

The Basidiomycetes microorganism can be cultivated principally by a conventional method for cultivating microorganisms. However, it is advantageous to use liquid culture media and cultivate under mild conditions with stirring and aeration since the Basidiomycetes species are aerobic.

Raw material for culture media includes plant fibers such as bran, straw, rice bran, bagasse, saw dust, and soybean lees. More specifically, the extract of one or more plant fibers with hot water can be used advantageously.

As carbon sources, there can be used any of glucose, sucrose, maltose, saccharose, white sugar, black sugar, steep liquor, waste steep liquor, malt extracts, and the like.

As nitrogen sources, meat extracts, peptone, gluten meal, soybean powder, dry yeast, yeast extracts, ammonium sulfate, ammonium tartarate, urea, and the like can be used. If desired, it is also possible to add to the medium various additives such as inorganic salts, e.g., phosphates, table salt (Nacl), magnesium salts, manganese salts, calcium salts, iron salts, etc. and vitamins, e.g., inositol, vitamin B1 hydrochloride, L-asparagine, biotin, etc.

The conditions for cultivating the above-mentioned Basidiomeycetes microorganisms may be similar to those for medium temperature-requiring bacteria. For example, they can be cultivated at a temperature of 10° C. to 45° C., preferably 15° C. to 30° C., for 4 to 20 days, preferably 6 to 12 days, at pH 2 to 6.

To the mixture of the culture media and mycelia thus obtained may be added an enzyme such as cellulase, amylase, protease, pectinase, chitinase, etc. The mixture is allowed to react for 2 to 20 hours under the condition of an optimum temperature to macerate mycelia, followed by heating to inactivate the enzyme.

The mycelia residue is removed from the culture thus treated by centrifugation or a similar separation technique. Then, the supernatant is extracted with hexane; ether or chloroform, or eluted with water by column chromatography using a reversed-phase partition carrier such as octadecyl-silane (ODS (C18), etc.), polystyrene-based polymer (MCI gel CHP-20P (Mitsubishi Chemical), etc.), hydroxypropyl-dextran resin (Sephadex LH-20 (Pharmacia), etc.), or the like to remove lipids. The fraction eluted with water is concentrated, and the concentrate is dissolved in an appropriate amount of water, and addition of ethanol in an amount of 3- to 5-times the amount of water in the solution gives rise to white precipitates. The precipitates collected by, for example, centrifugation are treated with an ion exchange resin or the like to remove salts, proteins, etc. therefrom to obtain a neutral polysaccharide fraction. Then, the polysaccharide fraction is purified by gel filtration chromatography with polyacrylamide resin (Bio-gel P-2 (BIO RAD), etc.), dextran resin (Sephadex G-15 (Pharmacia), etc.), cellulose matrix (Cellulofine (Seikagaku Kogyo)), Toyopearl (HW-40F (Toso), etc.) or using an ultrafiltration membrane.

The polysaccharides of the present invention exhibit the properties suitable as biological response modifiers (BRM) and can be used as an immuno-enhancing agent or an immunoactivator.

Hereinafter, the present invention is described by way of examples. However, the present invention is not limited thereto.

[Preparation]
1) Cultivation:

*Lentinus edodes* subcultured in a solid medium (1% maltose, 0.2% peptone, 0.2% ammonium tartarate, and 1.5% agar) in a glass petri dish of 90 mm in diameter was inoculated in a 10-liter culture bottle containing 8 liters of a liquid medium (150 g of rice bran together with 800 ml of water was heated at 120° C. for 15 minutes and filtered, and 10 g of maltose, 2.5 g of peptone, and 2.0 g of ammonium tartarate were added together with an appropriate amount of water, pH 4.0). The contents were incubated at 20° C. for 7 days with aeration. Next, 8 liters of the culture broth were inoculated in a culture tank containing 300 liters of a liquid medium having the same composition as above. Cultivation was continued at 23° C. for 9 days with aeration and mild stirring.

2) Extraction, Separation and Purification:

The resulting mixture of the culture medium and mycelia was warmed to 90° C. After addition of 8 g of amylase and continued reaction for 3 hours, the reaction mixture was cooled down to 60° C. After addition of 15 g of cellulase and 15 g of protease, the mixture was allowed to stand at 55° C. for 10 hours. The reaction mixture was further heated at 120° C. for 20 minutes to inactivate the enzymes.

The thus treated culture medium was centrifuged to remove residual mycelia, and the supernatant was concentrated under reduced pressure to obtain 7.5 kg of the extract, which was subjected to column chromatography using MCI gel CHP-20P (Mitsubishi Chemical) as a carrier and deionized water as eluant. The fraction eluted with deionized water was concentrated. The residue was redissolved in 1.5 liters of deionized water. Then, 6 liters of ethanol was added thereto to give white precipitates. The mixture was, then centrifuged and the supernatant was removed. Similarly, the precipitates were dissolved in deionized water and 4-fold volume of ethanol was added. Then, the mixture was centrifuged and the supernatant was removed by decantation. This procedure was repeated twice. The precipitates thus obtained were treated with cation exchange resin Dowex 50w x-8 (H form) (The Dow Chemical Company), the portion which was not adsorbed and was eluted out with water was concentrated. This fraction was subjected to column chromatography using Sephadex G-15 (Pharmacia). The portion eluted in the void volume was evaporated to dryness under reduced pressure to obtain 600 g of the objective polysaccharide.

The physical and chemical properties of the product are as follows:

(1) Nature: a white amorphous powder, without taste and odor;
(2) Solubility: insoluble in alcohol, acetone, hexane, benzene, ethyl acetate, tetrachloromethane, chloroform and ether, and soluble in water, formamide, and dimethylsulfoxide;
(3) pH of aqueous solution: neutral;
(4) Component sugar: To a 1% aqueous solution of the compound was added sulfuric acid to a concentration of 1N and the resulting solution was heated at 100° C. for 3 hours.

The reaction mixture was neutralized with barium carbonate and centrifuged. Thin layer chromatography of the supernatant was carried out with the following four developing solvents. In each case, no sugar spot except for glucose was detected, showing that this compound is a polysaccharide consisting exclusively of glucose.

(i) Ethyl acetate:methanol:acetic acid:water=65:15:10:10
(ii) Ethyl acetate:isopropanol:water=65:23:12
(iii) n-Butanol:acetic acid:water=2:1:1
(iv) n-Butanol:pyridine:water=6:4:3;
(5) Molecular weight: The molecular weight of the compound was presumed to be 500 to 10,000 from an elution curve obtained by subjecting samples to gel filtration column chromatography (Sephadex G-25 and Sephadex G-50, Pharmacia) using dextran having a known molecular weight as a standard substance;
(6) Specific optical rotation: $[\alpha]_D(24° C.)=+112°$ to $+116°$;
(7) Color reaction: the complete hydrolysis product of the compound was positive to anthrone-sulfuric acid reaction, phenol-sulfuric acid reaction, and chromotropic acid-sulfuric acid reaction, but negative for biuret reaction, Lowry-Folin reaction, Elson-Morgan reaction, and iodo reaction;

(8) Melting point: showing no clear melting point;
(9) IR spectrum: absorption due to acetyl groups at 1740 cm$^{-1}$; and
(10) $^{13}$C-NMR spectrum: 172, 100–104, 76–78, 72–74, 70, 68, 61, 18 ppm;

As major peaks, those characteristic to α-1,4-glucan and acetyl groups are observed. Furthermore, a part (ca. 30%) of signals due to glucose C-1, C-3, and C-4 are shifted owing to the acetylation, thus confirming that this compound consists of (1→4) bonded α-D-glucose units and is represented by the following formula:

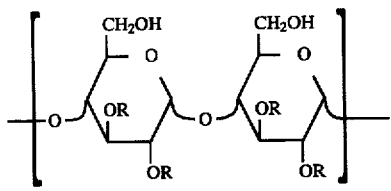

wherein R represents a hydrogen atom or an acetyl group in the ratio of 7:3 and that the compound is a novel polysaccharide which has a molecular weight of 500 to 10,000.

[Test Examples]

The following tests were intended to examine whether the novel polysaccharides of the present invention have properties of an immuno-enhancing agent (Biological Response Modifiers (BRM)) or not.

*Neutrophil leucocyte* accumulation:

Phagocytes such as *neutrophil leucocytes* and macrophages play an important role in homeostasis retention of the living body. They cover a wide variety of functions including anti-cancer or anti-microbial effects, inflammation, and antibody production as well as phagocytosis. The phagocytes tend to migrate toward and accumulate at the locations where foreign substances are present. In other words, substances which are foreign in nature to the living body cause phagocytes to accumulate. An immuno-enhancing agent (biological response modifier (BRM)) is a typical example thereof; it guides phagocytes that the support innate defense mechanism to local positions where it has been taken or administered so that they accumulate. The increment in the number of the phagocytes induces enhancement of the innate defense. That is, it can be understood that substances which guide phagocytes toward local positions have properties similar to immunological enhancing agents (BRM-like). Utilizing this phenomenon, tests were performed in order to examine whether the novel polysaccharides (APS) enhance the innate defense mechanism.

More particularly, a test sample was inoculated in the abdomen of a mouse, and accumulation of *neutrophil leucocytes* after 6 hours was examined. As shown in Table 1, abdominal cells in a control mouse incubated with physiological saline contained only a small amount, e.g., several % or less of *neutrophil leucocytes*. On the other hand, lentinan, which is a kind of BRM and used clinically as a cancerocidal agent, caused strong permeation such that the proportion of *neutrophil leucocytes* occupied 63% of the abdominal cells. The APS substance obtained in the example had strong *neutrophil leucocyte* accumulation activity of 75% higher than the known BRM.

TABLE 1

| Sample | Dose | Ratio of Accumulated Neutrophils |
| --- | --- | --- |
| Physiological saline | 1 ml/mouse | 2% |
| Lentinan | 1 mg/mouse | 63% |
| APS substance | 1 mg/mouse | 75% |

I claim:

1. A polysaccharide comprising (1→4) bonded α-D-glucose units represented by the following formula

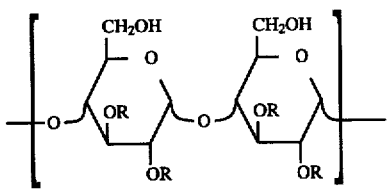

wherein R is a hydrogen atom or an acetyl group in a ratio of 7:3 of said polysaccharide having the following properties:

(1) Nature: a white amorphous powder, without taste and odor;

(2) Solubility: insoluble in alcohol, acetone, hexane, benzene, ethyl acetate, tetrachloromethane, chloroform and ether, and soluble in water, formamide, and dimethylsulfoxide;

(3) pH of aqueous solution: neutral;

(4) Component sugar: glucose only;

(5) Molecular weight: 500 to 10,000;

(6) Specific optical rotation: $(\alpha)_D(24°\ C.)=+112°$ to $+116°$;

(7) Color reaction: positive to anthrone-sulfuric acid reaction, phenol-sulfuric acid reaction, and chromotropic acid-sulfuric acid reaction, and negative to biuret reaction, Lowry-Folin reaction, Elson-Morgan reaction, and iodo reaction;

(8) Melting point: showing no clear melting point;

(9) IR spectrum: absorption specific to acetyl groups; and

(10) $^{13}$C-NMR spectrum: exhibiting signals characteristic to α-1,4-glucan and acetyl groups.

2. The polysaccharide as claimed in claim 1, wherein said polysaccharide is extracted and isolated from a culture medium in which a microorganism belonging to the class Basidiomycetes is cultured in the presence of a plant tissue extract.

3. The polysaccharide as claimed in claim 2, wherein said plant tissue extract is one or more plant fibers selected from the group consisting of bran, rice straw, rice bran, bagasse, saw dust, and soybean lees.

4. A method of preparing a polysaccharide having (1→4) bonded α-D- glucose units represented by the following formula

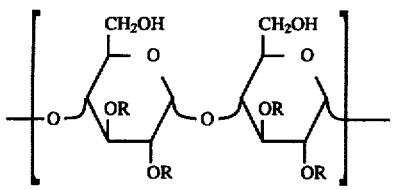

wherein R is a hydrogen atom or an acetyl group in a ratio of 7:3 of said polysaccharide having the following properties:

(1) Nature: a white amorphous powder, without taste and odor;

(2) Solubility: insoluble in alcohol, acetone, hexane, benzene, ethyl acetate, tetrachloromethane, chloroform and ether, and soluble in water, formamide, and dimethylsulfoxide;

(3) pH of aqueous solution: neutral;

(4) Component sugar: glucose only;

(5) Molecular weight: 500 to 10,000;

(6) Specific optical rotation: $(\alpha)_D(24°\ C.)=+112°$ to $+116°$;

(7) Color reaction: positive to anthrone-sulfuric acid reaction, phenol-sulfuric acid reaction, and chromotropic acid-sulfuric acid reaction, and negative to biuret reaction, Lowry-Folin reaction, Elson-Morgan reaction, and iodo reaction;

(8) Melting point: showing no clear melting point;

(9) IR spectrum: absorption specific to acetyl groups; and

(10) $^{13}$C-NMR spectrum: exhibiting signals characteristic to $\alpha$-1,4-glucan and acetyl groups, comprising the steps of:

cultivating a microorganism belonging to the class Basidiomycetes in a liquid culture medium in the presence of a plant tissue extract; and extracting and isolating the polysaccharide.

5. The method as claimed in claim 4 wherein said microorganism belonging to the class Basidiomycetes is selected from the group consisting of *Lentinus edodes, Agaricus bisporus, Grifola frondosa, Pholiota nameko, Pleurotus ostreatus, Flammulina velutipes, Ganoderma lucidum, Auricularia auricula, Ganoderma applanatum, Coriolus versicolor Grifola umbellata, Schizophyllum commune,* and *Volvariella volvacea.*

6. The method as claimed in claim 4, wherein said plant tissue extract is selected from the group consisting of one or more plant fibers selected from the group consisting of bran, rice straw, rice bran, bagasse, saw dust, and soybean lees.

7. The method as claimed in claim 6, wherein said plant tissue extract is a hot water extract of one or more of said plant fibers.

* * * * *

UNITED STATES PATENT AND TRADEMARK OFFICE
CERTIFICATE OF CORRECTION

PATENT NO. : 5,756,318
DATED : May 26, 1998
INVENTOR(S) : Kenichi Kosuna

It is certified that error appears in the above-identified patent and that said Letters Patent is hereby corrected as shown below:

Column 5, Line 7, delete "ca."

Column 5, Line 44, should read as follows: "thereof; it guides phagocytes that support the innate defense"

Signed and Sealed this

First Day of September, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO.   : 5,756,318
DATED        : May 26, 1998
INVENTOR(S)  : Kenichi Kosuna It is certified that error appears in the above-identified patent and that said Letters Patent is hereby corrected as shown below:

Column 5, Line 7 after "part ("   delete   "ca."

Signed and Sealed this

Twentieth Day of October, 1998

Attest:

BRUCE LEHMAN

Attesting Officer     Commissioner of Patents and Trademarks